United States Patent [19]

Morcher et al.

[11] 4,285,072
[45] Aug. 25, 1981

[54] ANTERIOR-POSTERIOR INTRAOCULAR LENS

[75] Inventors: Kurt A. Morcher, Stuttgart, Fed. Rep. of Germany; Leo H. Loones, Knokke-Heist, Belgium; Cornelius D. Binkhorst, Terneuzen, Netherlands

[73] Assignee: Harry H. LeVeen, Charleston, S.C.

[21] Appl. No.: 38,906

[22] Filed: May 14, 1979

[51] Int. Cl.³ .............................. A61F 1/16
[52] U.S. Cl. ............................................. 3/13
[58] Field of Search ................................. 3/13

[56] References Cited

U.S. PATENT DOCUMENTS

| 3,673,616 | 7/1972 | Fedorov et al. | 3/13 |
|---|---|---|---|
| 3,711,870 | 1/1973 | Deitrick | 3/13 |
| 3,866,249 | 2/1975 | Flom | 3/13 |
| 3,906,551 | 9/1975 | Otter | 3/13 |
| 3,913,148 | 10/1975 | Potthast | 3/13 |
| 3,922,728 | 12/1975 | Krasnov | 3/13 |
| 3,925,825 | 12/1975 | Richards et al. | 3/13 |
| 3,971,073 | 7/1976 | Richards et al. | 3/13 |
| 3,975,779 | 8/1976 | Richards et al. | 3/13 |
| 3,979,780 | 9/1976 | Boniuk | 3/13 |
| 3,986,214 | 10/1976 | Krasnov | 3/13 |
| 3,996,626 | 12/1976 | Richards et al. | 3/13 |
| 3,996,627 | 12/1976 | Deeg et al. | 3/13 |
| 4,010,496 | 3/1977 | Neefe | 3/13 |
| 4,014,049 | 3/1977 | Richards et al. | 3/13 |
| 4,041,552 | 8/1977 | Ganias | 3/13 |
| 4,053,953 | 10/1977 | Flom et al. | 3/13 |
| 4,056,855 | 11/1977 | Kelman | 3/13 |
| 4,073,014 | 2/1978 | Poler | 3/13 |
| 4,073,015 | 2/1978 | Peyman et al. | 3/13 |
| 4,077,071 | 3/1978 | Freeman | 3/13 |
| 4,079,470 | 3/1978 | Deeg et al. | 3/13 |
| 4,087,866 | 5/1978 | Choyce et al. | 3/13 |
| 4,110,848 | 9/1978 | Jensen | 3/13 |
| 4,159,546 | 7/1979 | Shearing | 3/13 |

*Primary Examiner*—Clifford D. Crowder
*Attorney, Agent, or Firm*—Gipple and Hale

[57] ABSTRACT

An intraocular lens and method for implanting the same in the posterior chamber of an eye having a posterior capsule. The lens has a lens support system including anterior supports which allows it to be placed in the anterior chamber of the eye against the iris and posterior supports which extend down into the posterior chamber and capsule for capsular fixation. After capsular fixation has occurred the pupil and iris of the eye is dilated, so that the anterior supports do not engage the iris. Upon reconstriction of the pupil the iris rides back over the anterior supports and over the face of the lens, positioning the lens in the posterior chamber with the lens being mounted in the chamber by the support system.

17 Claims, 21 Drawing Figures

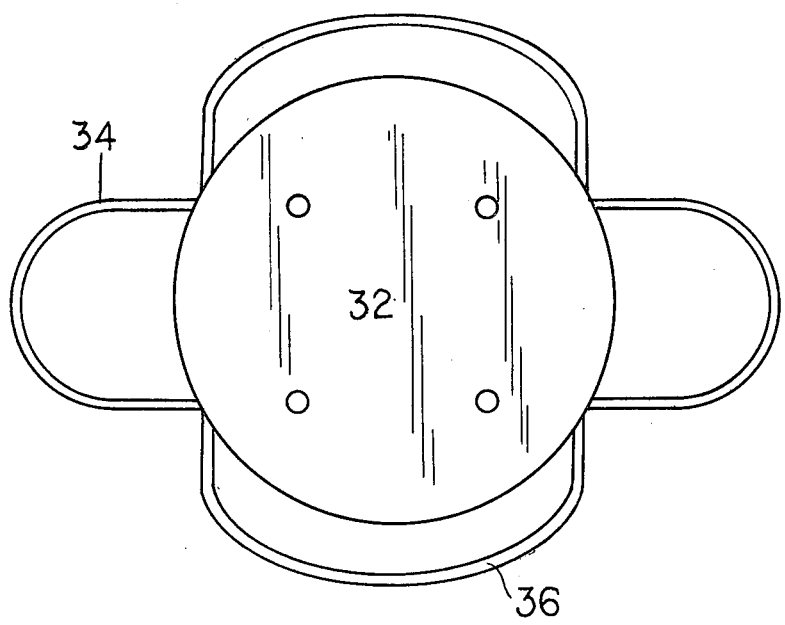
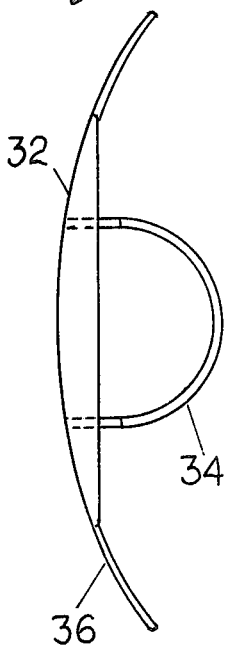
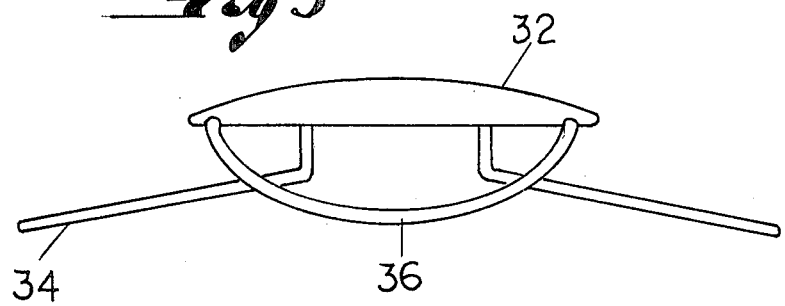

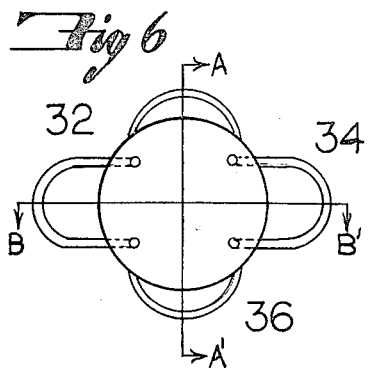
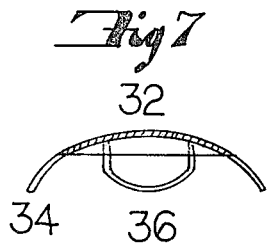
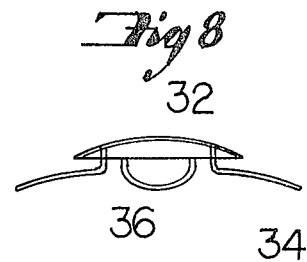
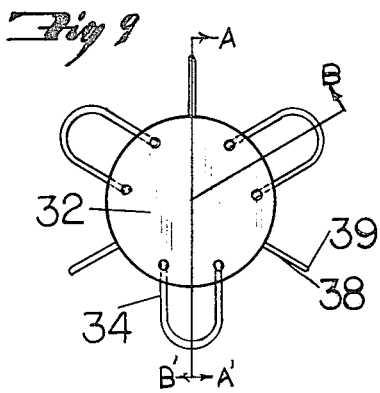
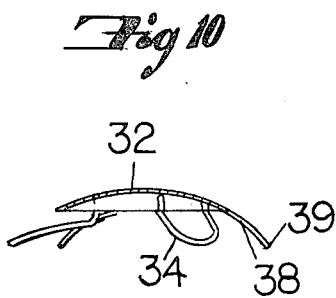
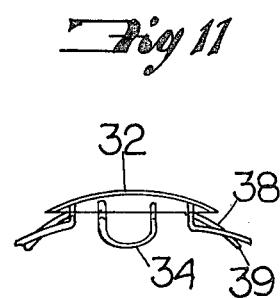
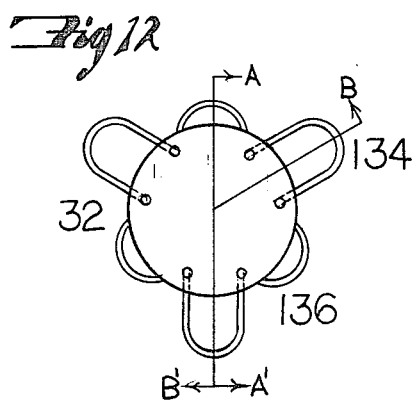
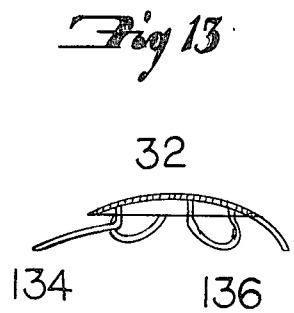
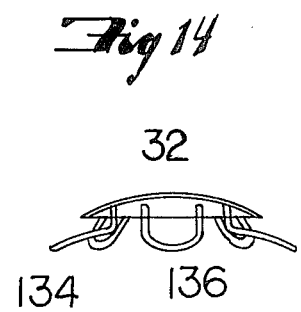
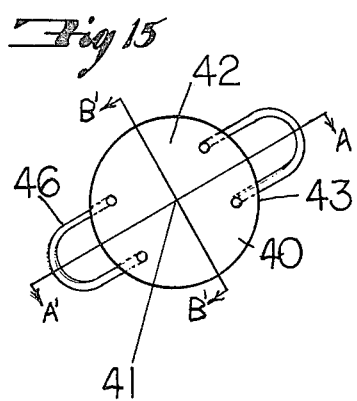
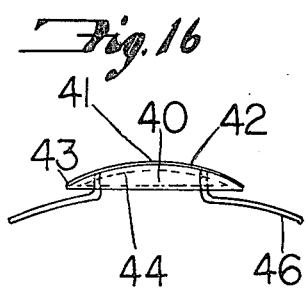
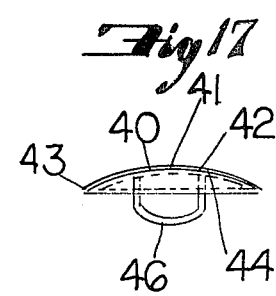

ANTERIOR-POSTERIOR INTRAOCULAR LENS

FIELD OF THE INVENTION

This invention relates to a method for implanting an artificial intraocular lens in the posterior chamber of the eye and a novel lens construction including retaining means which allows seating of the lens in the posterior chamber.

DESCRIPTION OF THE PRIOR ART

When no lens is present in the eye, which is known as the aphakic condition of aphakia and is usually the result of intracapsular or extracapsular lens extraction, the eye does not have the ability to focus rays of light. Therefore, the eye receives a blurred image and vision is impaired.

The most common solution for providing a focusing mechanism to obviate the aphakic condition is to interpose contact lenses or spectacles or a combination thereof between the eye and the light entering therein. However, both contact lenses and spectacles have drawbacks when used in the treatment of aphakia. Neither spectacles nor contact lenses can duplicate the natural optical system because they are positioned outside of the eye, which results in a shift of the optical center from the vivo state. Because the optical center has been shifted, the image received by the eye is changed in size. Many aphakic patients who have had their cataracts removed are fitted with glasses or spectacles. These extremely thick lenses present many more problems than they solve. Immediately upon receiving cataract spectacles a patient is confronted with the problem of a remarkable increase in the size of familiar objects. Cataract spectacles magnify objects by up to 35 percent, so that all objects appear much larger than actual size, which may take many weeks for patient adjustment to the condition. If only one cataract is removed from a patient, the patient must thereafter wear a combination of a one cataract spectacle for the operated eye and a regular spectacle for the unoperated eye. Thus the patient will find it impossible to fuse the different size images seen by each eye into one picture, resulting in double vision. Even when both eyes have been operated on and spectacles are provided for both eyes, the patient still experiences a partial element of false orientation in that everything seems closer than it previously appeared.

Another problem faced by the wearer of spectacles is that the all straight lines of the outside world are transformed into curves, and whenever a patient moves his or her eyes the curves seem to squirm, which requires the wearer to hold the eyes still and look only through the optical center of the cataract lens glass. Thus the wearer must turn his or her head and not move the eyes in order to see anything not directly in front of them. Furthermore, the wearer is confronted with a ring-like zone within which no image appears causing what is called the "jack-in-the-box phenomena" where people and objects pop in and out of view as they pop in and out of the blind area, thus causing the wearer to have collisions with anything interjecting itself into the blind area. In addition to the aforementioned problems, spectacles must be taken off for activities such as washing a person's face, swimming or sleeping, causing the wearer to fumble in the morning until he or she can find their glasses. Another common problem is that the wearer often misplaces the spectacles and must resort to obtaining a new pair or pairs of spectacles which can be extremely expensive and disturbing to cataract patients. Still another problem is that cataract spectacles must be accurately centered and adjusted in order to see clearly and well. This means that the optical formulation must also be available to the wearer so that new glasses can be made.

Contact lenses are superior to thick cataract spectacles since the wearer enjoys good peripheral side vision. The magnification problem does not bother contact lens wearers as much as it does cataract spectacle wearers, because the contact lenses only magnify in the range of 7 to 10 percent. Furthermore, hand to eye coordination of contact lens wearers is better than in spectacle wearers, as objects are seen in more normal spatial orientation and straight lines are not seen as curves. However, contact lenses are very small and fragile, and it is difficult to insert and remove them daily, particularly for elderly users or individuals with arthritis or coordination problems. In addition allergies and dry eye conditions also interfere with contact lens wearing. Furthermore, patients who have had a cataract removed only from one eye may have a problem of adjusting to two different sized images, as seen by the two eyes causing double vision.

Intraocular lens provide a significant improvement over the previously used artificial ocular aids in that once the implantation has been implemented patients regain a close approximation of their former visual function. The wearers of intraocular lens implants regain full side to side vision and problems of magnification and depth perception are practically non-existent. Since the intraocular lens are permanently implanted within the eye, problems of daily cleaning, insertion and removal, and loss and replacement are eliminated. Furthermore, the wearer can enjoy sports such as swimming as the lenses remain in the eye and cosmetically there is no difference between persons who have intraocular lenses and those persons who have had no history of cataracts or eye surgery.

The most common reason for removal of a lens is the condition of lenticular opacity known as a cataract, which occurs primarily in aged persons.

Cataracts are the leading cause of blindness, and more than 400,000 persons in the United States undergo surgery for the removal of diseased lenses in their eyes each year.

The most promising method of sight restoration for cataract patients is the intraocular lens. An intraocular lens (hereinafter referred to as an IOL) in various parts of the specification is one which is placed inside the eye. When the IOL is implanted in substantially the same location formerly occupied by the natural lens, relatively normal vision may be restored to the patient. Generally lens implantation and cataract surgery takes around 45 minutes to an hour and with the lens implant the person usually has improved vision within a couple of days, and continued improvement over several more weeks until the eye is completely healed.

The desirability of implanting an artificial lens within the eye to obviate the condition of aphakia was first proposed by Tardini in 1764. The first actual lens implant was carried out by Dr. Harold Ridley in 1949.

Ridley originally placed this lens in the posterior chamber of the eye behind the iris, resting against the ciliary body between the ciliary processes and the base of the iris. However, positioning of this lens in the posterior chamber was abandoned because of instances of dislocation after implantation and failures from glaucoma and the like.

One of the problems encountered with the early lens implants was the tendency for some lens to partially or totally dislocate from the original position of insertion. This stimulated many alternate designs to keep the IOL centered along the optic axis with positions varying from (1) in front of the pupilary space (anterior chamber); (2) within the pupilary space (iris plane) or (3) just posterior to the pupilary space (posterior chamber).

Ridley's failure with posterior chamber artificial lenses led him and others, such as D. P. Choyce, to turn their attention to IOL's implanted in the anterior chamber of the eye between the iris and the cornea. The particular lens used had radially protruding feet which accomplished positioning of the lens in front of the pupil. These efforts met with limited success, primarily because of the problems of irritation of the eye by the supporting feet.

It should be noted that placement of the lens in the anterior chamber is an unnatural position. Also, an anterior chamber lens is not positioned adjacent to the hyaloid membrane supporting the vitreous humor, and instances of forward displacement of the vitreous humor and retinal detachment are more likely to occur when anterior chamber lenses are used.

Binkhorst has developed an iris-clip (four-loop) lens and an irido-capsular (two or three-loop) lens. Both lenses comprise a lens of larger diameter than the pupil and are placed so that the periphery of the lens engages the front of the iris. The iris-clip (four loop) lens is held by two pairs of loops which flank the iris and support the lens in front of the pupil. In some instances, the iris is sutured to the clips to secure the positioning of the lens. The irido capsular (two or three-loop) lens has two or three loops which protrude from the back of the lens and extend posteriorly behind the iris to engage the capsula of the crystal lens that is left inside the eye after extracapsular cataract extraction. Both designs of lenses being in the perpupiliary position and having supports that extend posteriorly behind the iris, are unsatisfactory because, by necessity, it interferes with constriction of the pupil and fixes the size of the pupil.

Lenses which are placed in the anterior chamber come in various configurations, and are secured to the iris by various methods are shown in U.S. Pat. Nos.: 3,673,616; 3,906,551; 3,922,728; 3,925,825; 3,971,073; 3,975,779; 3,979,780; 3,986,214; 3,996,627; 4,010,496; 4,056,855; 4,073,015; 4,077,071; 4,079,470 and 4,087,866.

Artificial lenses designed for positioning in the posterior chamber are described in U.S. Pat. No. 3,711,870 to Deitrick. Deitrick's lens comprises a central optical position surrounded by a resilient silicone flange shaped to receive and nest against the ciliary body. The lens is held in place by suturing the resilient flange to the ciliary body. Another lens shown by U.S. Pat. Nos. 3,925,825 and 4,014,049 to Richards et al. is designed for implantation in either the anterior or posterior chamber of the eye, with the lens supporting (haptic) section of the IOL comprising a plurality of flexible spring like members designed to follow the margin of the dynamic pupil, while providing longitudinal fixation and centration of the lens. The U.S. Pat. Nos. 4,053,953 and 3,866,249 to Flom disclose a posterior lens held in place by an insertion necklace in the former and a holding ring in the latter. In U.S. Pat. No. 4,041,552 to Ganis the lens element is placed in the posterior chamber and supported by support on the anterior side of the iris, while a lower arm is sutured to the ciliary body and sclera at one side of the iris with another arm extending to the opposite side.

U.S. Pat. No. 3,913,148 to Potthast discloses a lens apparatus inserted in the posterior chamber, with a plurality of cantilevered clips, each of which is mounted to a central portion which extends outward from the face of the lens towards the periphery. The clips are used to secure the iris to the front face of the lens when the lens is positioned within the posterior chamber of the eye behind the iris.

Several of the prior art lenses are discussed in an article by D. P. Choyce entitled "History of Intraocular Implants" which is printed in Annals of Opthalmology, October, 1973. The article also includes a list of references from which further information concerning prior art intraocular lenses can be obtained.

SUMMARY OF THE INVENTION

The present invention pertains to a novel lens design and method for implanting an IOL that encompasses the advantages of capsular support and fixation, together with the advantages of the posterior chamber position of the optical portion of the lens thus including the advantages of excellent centration of the lens by having the optic portion of the IOL temporarily occupy a pre-pupilary or anterior chamber position allowing pupilary constriction to center the entire lens structure. A capsular support is where the posterior capsule of the crystalline lens which was left in place after extra-capsular surgery supports the support system of the lens. Thus the lens is implanted into the eye so that the design incorporates the characteristic of centration by pupilary constriction while the optic portion of the lens rests in the anterior chamber in the pre-pupilary position. After the capsular fixation occurs between the posterior loops of the support system in the posterior capsule (usually within 4 to 5 days) the pupil is dilated and the optic portion of the IOL moves into the posterior chamber as the pupil is reconstricted.

The optical portion of the IOL is of normal lenticular design with posterior loops attached to the design to go into the capsular bag. Anteriorly there are attached loops or extension members that hold the optic portion of the lens within the anterior chamber for pupilary centration until capsular fixation has occured. These anterior loops or extensions extend outward and posteriorly so that after capsular fixation of the eyewell and pupilar dilation is completed, the pupil and iris dilates and moves away from the optical portion by slipping out from under the anterior loops or extensions. When the pupil is reconstricted again the iris slides up and over the anterior extensions and front surface of the IOL moving it to a permanent location within the posterior chamber. The invention thus provides a posterior chamber lens which has advantages as previously discussed over anterior chamber lenses. The underlying principle of the anterior-posterior chamber lens uses the sphinter muscles for centration avoiding surgical manipulation such as iris sutures and avoiding the ciliary sulcus which has a potential danger for late complications. The iris sphinter muscle is used for centration only for a short period until capsular fixation is accomplished. The sphincter muscle is dismissed from its duty as the lens and the supports are constructed with short anterior extensions which extend posteriorly, so as to allow the lens to slip from the anterior chamber to the posterior chamber through dilation and subsequent constriction of the pupil fixing the lens in its final position. The lens is an initial anterior chamber lens and its final position is that of a posterior chamber lens. Its two plane design prevents contact of the lens with the posterior capsule, and creates room for spontaneous absorption of critical cortical material and aspiration of cortical material and for incision of a capsular membrane if later necessary. Thus it does not force the surgeon to do a primary needling because of lack of adequate room for discission. The transition of the lens from the anterior chamber to the posterior chamber is achieved through a novel design of extension loops or haptics which allow seating of the lens through pupilary dilation. The lens is a capsular bag fixated lens situated finally in the posterior chamber without iris involvement. It supports the iris as the crystalline lens does, avoiding iridodonesis and its long term consequences of pigmentary dispersion and corneal endotheliel cell loss.

Thus the anterior-posterior chamber IOL provides normal pupilary mobility, lack of pupilary erosion, no pseudo-phakodonesis, very little or no iridodonesis, less glare from lens edges and loops and is closer to the optical center. The novel lens also provides less aniseikoma with less residual refractive error and eliminates iris sutures while combining the advantages of capsular fixation and the advantages of anterior chamber or prepupilary centration. Esthetically the lens is also much more similar to the normal crystaline lens in appearance, so that cosmetic benefits are also derived along with the medical benefits.

The above-mentioned purposes and operations of the invention are more readily apparent when read in conjunction with the following description of the drawings and the detailed description of the preferred embodiment of the present invention.

BRIEF DESCRIPTION OF THE DRAWINGS

FIG. 3 is an enlarged top plan view of the preferred embodiment of the anterior-posterior chamber IOL;

FIG. 4 is a side elevational view of the IOL shown in FIG. 3;

FIG. 5 is a front elevational view of the IOL shown in FIG. 3;

FIG. 6 is another top plan view of the IOL shown in FIG. 3;

FIG. 7 is a cross-sectional view taken along lines A-A' of FIG. 6; FIG. 8 is a cross-sectional view taken along lines B-B' of FIG. 6;

FIG. 9 is a top plan view of another embodiment of the anterior-posterior chamber IOL;

FIG. 10 is a cross-sectional view taken along lines A-A' of FIG. 9;

FIG. 11 is a cross-sectional view taken along lines B-B' of FIG. 9;

FIG. 12 is a top plan view of yet another embodiment of the anterior-posterior chamber IOL;

FIG. 13 is a cross-sectional view taken along lines A-A' of FIG. 12;

FIG. 14 is a cross-sectional view taken along lines B-B' of FIG. 12.

FIG. 15 is a top plan view of still another embodiment of the anterior-posterior chamber IOL;

FIG. 16 is a cross-sectional view taken along lines A-A' of FIG. 15;

FIG. 17 is a cross-sectional view taken along lines B-B' of FIG. 15;

DETAILED DESCRIPTION OF THE DRAWINGS

Figure 1:
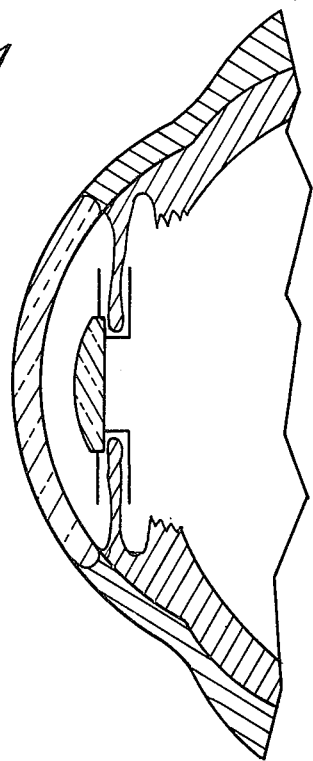
FIG. 1 is a cross-sectional view of a prior art anterior chamber lens supported by the iris.
Figure 2:
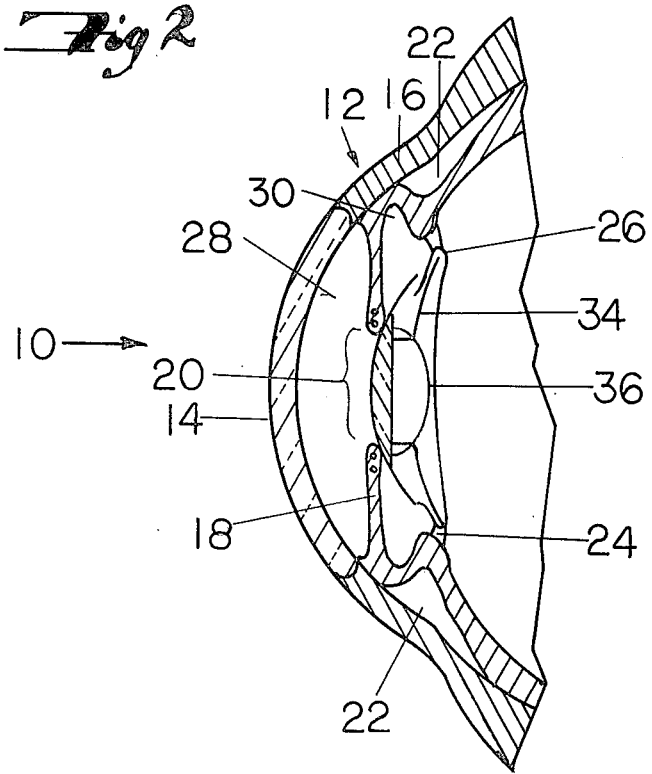
FIG. 2 is a cross-sectional view of the inventive anterior-posterior intraocular lens mounted in the eye in the posterior chamber.

The present invention and more particularly the preferred mode of the invention is shown in FIGS. 2 through 8, 18 and 19 and is directed towards an IOL 10 and a method for implanting the IOL in an eye 12.

An eye 12 which has undergone extracapsular surgery is shown in FIGS. 2 and 18 through 21. The eye 12 shown with an illustrated cornea 14, sclera 16, iris 18, pupil 20, ciliary muscle 22, ciliary processes 24 and posterior capsule 26 which was left in place after extracapsular surgery.

The eye 12 is divided into two chambers; an anterior chamber 28 located in front of the iris and a posterior chamber 30 located behind the iris. The lens 32 is a capsular bag fixated lens and while the preferred embodiment discloses the lens 32 as plano-convex in structure, it can under desired circumstances be double convex and be provided with spherical, toric or aspherical curvatures. The lens is made of a material which is biologically inert and is not susceptible to being absorbed by the human fluids and capable of being tolerated by the human body when implanted. Such materials which can be used are quartz, ophthalmic glass, methylmethacrylate resins such as those available under the trade names "perspex", "lucite" and "plexi-glass" along with biologically natural, chemically pure polymethacrylates or biologically inert polymerised materials. Examples of lens glasses which can be used which are chemically durable, free of toxicity, harmful radioactivity with low density and lightness of weight with a transmission for simulating the optical absorption of the human crystal lenses are the various glasses set forth in U.S. Pat. No. 3,996,627 which patent is incorporated by reference into this application.

In the preferred embodiment and best mode of the invention posterior loops 34 are attached to the lens 32 and designed to extend into the capsular bag. Positioned anteriorly on the lens and orientated 90° to the posterior loops 34 are loops or extension members 36. These loops hold the optical portion of the lens within the anterior chamber of the eye for pupilary centration until the capsular fixation of the posterior loops 34 has occurred. These anterior loops or extension members 36 extend outward and posteriorly in such a manner as to end in the same general plane as the outward extension of the posterior loops. After capsular fixation of the eyewell and pupilary dilation is completed the pupil 20 and iris 18 dilates and moves away from the optical portion of the lens slipping out from under the anterior loops 36. When the pupil 20 is constricted again the iris 18 slides up and over the anterior loops 36 and the front surface of the lens 32 moving it into a permanent location within the posterior chamber. The supporting system haptics or loops may be described as being formed of "wire" it being understood that the term "wire" used in this specification is intended to include resilient strands, strips, or rods of biologically inert material, whether such material is metallic or plastic and/or whether one or the other is used exclusively throughout the system. Acceptable materials which avoid irritation in the body and rejection such as platinum, titanium, and extruded polyamide such as nylon or a polyolefin such as polypropolene may be used.

Thus the embodiment of FIGS. 12 through 14 is similarly constructed to the preferred embodiment excepting that it uses three anterior loops 136 and three posterior loops 134 equidistantly spaced as compared to the two pairs of opposing loops of the preferred embodiment.

In the embodiment shown by FIGS. 9 through 11 the anterior loops are replaced by extending rod like members 38 with smoothly rounded termini 39. If desired the termini may be spherically shaped. These extending anterior members 38 extend posteriorly away from the lens 32 toward the posterior capsule.

Yet another embodiment is disclosed in FIGS. 15 through 17 in which a lens 40 having a convex surface 42 and concave surface 44 is disclosed. The lens surface itself takes the place of the anterior clips or loops of the preferred embodiment. It should be noted in this embodiment that the central midpoint 41 of the lens is positioned so that its rounded peripheral edges 43 extend posteriorly away from the central midpoint. This lens is provided with a pair of posterior loops 46 which extend outward posteriorly in the same manner as the preferred embodiment and which serve in the same function as the posterior loops of the preferred embodiment.

In the implantation of the anterior-posterior chamber lens the posterior loops 34 and 46 attached to the lens are designed to go into the capsular bag 26 with the anterior loops or extensions 36 holding the optical portion of the lens within the anterior chamber with pupilary centration until capsular fixation has occurred. The feet of the posterior loops dig into the capsular bag and are held in place in the bag. Capsular fixation occurs between the posterior loops 34 or support system and the capsular bag usually within four or five days. The anterior loops or extensions extend outward and posteriorly in such a fashion as to end in the same general plane or level of the posterior loop, so that after capsular fixation of the eyewell the pupil is dilated. Upon pupilary dilation the iris dilates and moves away from the optical portion slipping out from under the anterior loops. When the pupil is constricted again the iris 18 now slides up and over the anterior loops 36 and the front surface of the intraocular lens, thus moving it to its permanent position within the posterior chamber. Thus the anterior and posterior loops act as a spring mechanism locking the lens in a fixed position.

Figure 18:
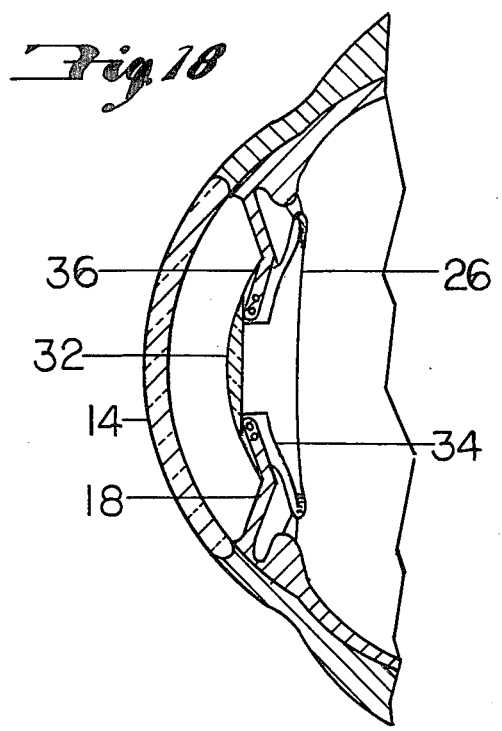
FIG. 18 is an enlarged cross-sectional view of the preferred embodiment of the lens placed in the eye during an implant in the anterior chamber.
Figure 19:
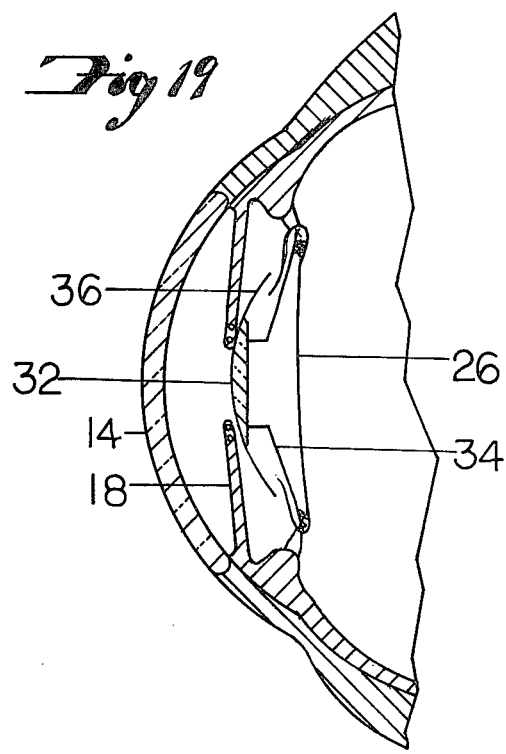
FIG. 19 is a cross-sectional view of the lens shown in FIG. 18 after dilation and reconstriction of the pupil and after centration of the lens with the lens being placed in position in the posterior chamber.
Figure 20:
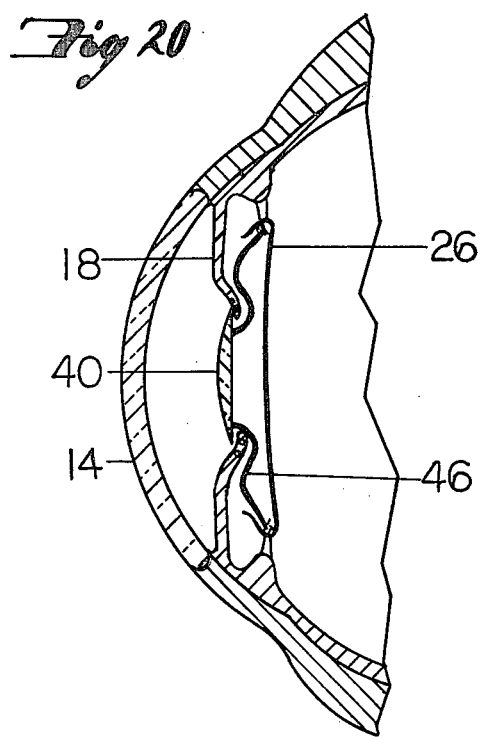
FIG. 20 is an enlarged cross-sectional view of the embodiment of FIGS. 15-17 of the invention placed in the anterior chamber of the eye.
Figure 21:
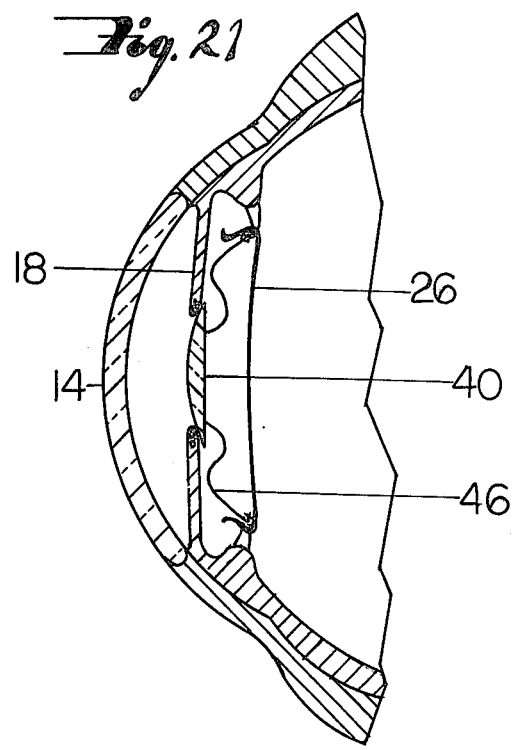
FIG. 21 is a cross-sectional view of the invention shown in FIG. 20 after the pupil has been dilated and reconstructed after centration of the lens with the lens being positioned in the posterior chamber after constriction of the pupil.

The present invention is used after extracapsular surgery in connection with the posterior capsule 26 of the crystalline lens. The new lens embodiment encompasses the advantages of capsular support and fixation, together with the advantages of posterior chamber positioning of the optical portion of the lens 32. After extracapsular surgery the lens is placed in the eye for centration by having the optic portion of the IOL temporarily occupy a prepupilary or anterior chamber position allowing pupilary constriction to center the entire IOL structure. The optic portion of the lens is held in the anterior chamber by the anterior loops 36 which extend out over the iris as shown in FIG. 18. The anterior loops 36 or extension members 38 extend outward from the lens a shorter distance than the posterior loops 34 and are directed posteriorly so that after pupilary dilation is accomplished the pupil and iris move away from the optical lens portion slipping out from under the anterior loops 36 or extension members 38. When the pupil is reconstricted the iris slides up and over the anterior loops 36 or extension members 38 and the front surface of the lens 32 supporting the iris and moving the lens to a permanent location within the posterior chamber as shown in FIG. 19. The lens is in effect spring loaded in the eye.

It will be appreciated that the embodiment shown in FIGS. 15 through 17 that the curved lens body 42 with its rounded periphery 43 acts in the same manner as the anterior loops 36 or extension members 38 of the other embodiments.

While the preferred embodiment of the invention has been disclosed, it is understood that the invention is not limited to such an embodiment since it may be otherwise embodied in the scope of the appended claims.

What is claimed is:

1. An intraocular lens adapted to be implanted in an eye having a posterior capsule comprising an optical lens and support system means connected to said lens, said support system means comprising a plurality of posteriorly projecting members extending from said lens a predetermined distance necessary to extend into the posterior capsule for capsular fixation and a plurality of anterior clips extending posteriorly from the rear surface of said lens and extending outward from said lens a predetermined distance greater than a pupil of the eye as normally constricted but less than the pupil of the eye when substantially fully dilated, said support system being adapted to hold said lens centered on the pupil in the anterior chamber of the eye until natural fixation of said posteriorly projecting members occurs at which time the pupil is dilated and the iris moves away from the anterior members so that said anterior members of said lens are positioned in the posterior chamber of the eye.

2. A lens system as claimed in claim 1 wherein said plurality of members are loops.

3. A lens system as claimed in claim 1 wherein said plurality of anterior members are loops.

4. A lens system as claimed in claim 1 wherein said plurality of anterior members are linear members.

5. A pseudophakos for implantation in an eye which has undergone extracapsular surgery comprising a lens having an optically finished surface, a plurality of slender and resilient support arms affixed to said lens, said arms being of a looped configuration with at least two of said arms being posterior arms extending rearward of said lens through the pupil of said eye to engage the posterior capsule for capsular fixation, and at least two of said arms being anterior arms positioned forward of said pupil and extending posteriorly so that the lens is positioned in the anterior chamber of the eye and held to an iris, allowing said lens to be engaged by the normal muscle action of the sphincter muscle of the iris and optically centered by such muscle action said anterior arms extending outwardly and rearwardly a predetermined distance sufficient to allow said lens to be moved to the posterior chamber of the eye after the iris has been dilated.

6. A pseudophakos as claimed in claim 5 wherein one of said sides of said lens is planar and the other side is convexly curved.

7. A pseudophakos according to claim 6 wherein said lens is formed of glass.

8. A pseudophakos according to claim 6 wherein said lens is formed of a plastic material.

9. A pseudophakos according to claim 5 wherein said rearwardly extending arms are mounted in the rear planar surface of said lens body and extend angularly from said planar surface away from the optic path of said lens.

10. An intraocular lens for use after extracapsular surgery of an eye comprising a lens having an uninterrupted, optically finished convex anterior side and a planar posterior side, a plurality of posterior clips extending rearwardly of said planar surface and angled away from the optic axis of the lens for fixation of the lens in a posterior capsule, a plurality of anterior clips extending posteriorly from the planar surface of said lens and extending outward from said lens a predetermined distance greater than a pupil of the eye as normally constricted but less than the pupil of the eye when substantially fully dilated, said anterior clips extending from the optic axis of the lens a lesser distance than said posterior clips, said anterior clips holding the lens in an anterior chamber against an iris when the pupil is normally constricted while allowing the lens to be transported into a posterior chamber when the pupil is substantially fully dilated and reconstricted.

11. An optical lens having means for centering said lens in the posterior chamber of an eye between a posterior capsule left after extracapsular surgery and the iris, said means comprising at least two base supporting loops adapted to extend posteriorly of said iris and engage said posterior capsule, said loops extending in opposite directions from each other and fastened to one side of said lens within the peripheral edge of said lens and a plurality of equally spaced extending rod members fastened to said lens, said rod members extending outward from said lens a predetermined distance past the periphery of a pupil of the eye as normally constricted but within the periphery of the pupil of the eye when substantially fully dilated, said rod members allowing said iris when thereafter reconstricted to run over said rod members to engage the front portion of the lens seating said lens in a fixed optical alignment.

12. An intraocular lens apparatus for insertion in the posterior chamber adjacent the iris comprising a lens having a convex front face, a concave rear face and a rounded periphery, a plurality of cantilevered clips mounted to said rear face and extending outwardly and posteriorly from said face, said clips being adapted to secure the lens to a posterior capsule left in place after extracapsular surgery, said lens being positioned within the anterior chamber of the eye with its periphery and rear face mounted on an iris, at least two of said clips comprising anterior clips extending outwardly and rearwardly a predetermined distance sufficient to allow said lens to be moved to the posterior chamber of the eye after the iris has been dilated so that the front face engages the iris when said lens is positioned within a posterior chamber of said eye immediately behind said iris.

13. A surgical method of replacing the natural lens of an eye with an artificial intraocular lens having a support system comprising the steps of:
 a. removing the natural lens leaving a posterior capsule;
 b. placing the lens in the anterior chamber of the eye adjacent the iris with part of the support system engaging the iris and a second part of the support system extending through the pupil to engage the posterior capsule a predetermined number of days so that capsular fixation occurs between said second part of the support system and the posterior capsule;
 c. dilating the pupil of the eye from its normal state so that the pupil is wider than the support system engaging it; and
 d. reconstricting the pupil so that the iris engages and moves the artificial intraocular lens into the posterior chamber.

14. A method of implanting a pseudophakos including a support system in an eye after extracapsular surgery has left a posterior capsule of the lens in place, comprising the steps of:
 a. placing the pseudophakos in a fixed position in the anterior chamber of the eye adjacent said iris with a portion of said support system extending through the pupil of said iris to contact said posterior capsule until capsular fixation occurs between the support system and the posterior capsule of the lens;
 b. dilating the iris until the pupil expands; and
 c. constricting said iris and pupil causing said iris to override said pseudophakos positioning said pseudophakos in the posterior chamber of said eye in a fixed position.

15. An intraocular lens adapted to be implanted in the anterior chamber of an eye following extracapsular cataract removal for ultimate placement in the posterior chamber of said eye, said lens comprising a disk-like optical lens; a plurality of anterior support members, said anterior support members being attached to said disk-like optical lens adjacent the periphery of said optical lens, said anterior support members extending outwardly and rearwardly from said optical lens a predetermined distance greater than the periphery of a pupil of the eye as normally constricted but less than the periphery of the pupil of the eye when substantially fully dilated; a plurality of posterior support members, said posterior support members being attached to the rear of said optical lens, said posterior support members extending rearwardly from said optical lens for a distance sufficient to pass through said pupil when said pupil is constricted to a normal radius, said posterior support members extending outwardly for a distance greater than the radius of said pupil when said pupil is maximally dilated sufficient to contact and stimulate the natural fixation at the periphery of an extra-capsular bag in said posterior chamber; said anterior support members being less than the length of said posterior support members allowing said iris to pass over said anterior support members when said pupil is maximally dilated, said pupil when reconstricted engaging said lens.

16. An interocular lens as claimed in claim 15 wherein the mid point of each anterior member is positioned approximately 60 degrees from the mid point of the adjacent posterior member.

17. An interocular lens as claimed in claim 15 wherein the mid point of each anterior member is positioned approximately 90 degrees from the mid point of the adjacent posterior member.

* * * * *